United States Patent [19]

Liebetruth

[11] 4,174,481

[45] Nov. 13, 1979

[54] TOMOGRAPHIC X-RAY APPARATUS FOR THE PRODUCTION OF TRANSVERSE LAYER IMAGES

[75] Inventor: Reiner Liebetruth, Erlangen, Fed. Rep. of Germany

[73] Assignee: Siemens Aktiengesellschaft, Berlin & Munich, Fed. Rep. of Germany

[21] Appl. No.: 775,452

[22] Filed: Mar. 8, 1977

[30] Foreign Application Priority Data

Mar. 31, 1976 [DE] Fed. Rep. of Germany ....... 2613809

[51] Int. Cl.$^2$ ............................................. G03B 41/16
[52] U.S. Cl. .......................... 250/445 T; 250/416 TV; 250/491
[58] Field of Search ............ 250/445 T, 416 TV, 360, 250/358 R, 491

[56] References Cited

U.S. PATENT DOCUMENTS

| 3,974,388 | 8/1976 | Distler | 250/445 T |
| 4,047,044 | 9/1977 | Weaver | 250/416 TV |
| 4,051,379 | 9/1977 | Zacher | 250/416 TV |

*Primary Examiner*—Craig E. Church
*Attorney, Agent, or Firm*—Hill, Van Santen, Steadman, Chiara & Simpson

[57] ABSTRACT

In order to facilitate exact positioning of a patient relative to tomographic X-ray apparatus the patient is moved longitudinally of the apparatus and the apparatus is retained in a limited angular relationship and operated to produce successive sets of transmittance readings to define a radiographic image having a longitudinal extent sufficient to encompass the precisely desired region of the patient for which a tomographic image is to be generated. The stored sets of readings may be reproduced on a conventional television display unit along with suitable reference means coordinated with the patient's longitudinal position in the apparatus. The radiograph even though taken in a single angular relationship can still provide sufficient information to permit selection of the precise desired patient longitudinal position relative to the tomographic apparatus, whereupon the tomographic apparatus is operated in the usual manner for scanning of the selected transverse layer over a wide range of angles but with a fixed relative longitudinal relationship. Advantageously, the scanner may present a fan-type beam which in a fixed angular relationship to the patient still scans a substantial portion of the patient cross section, the X-ray source or sources being pulsed at successive longitudinal positions of the patient relative to the scanning apparatus, and the successive sets of readings being utilized for on line display of a radiograph covering the desired longitudinal extent.

3 Claims, 2 Drawing Figures

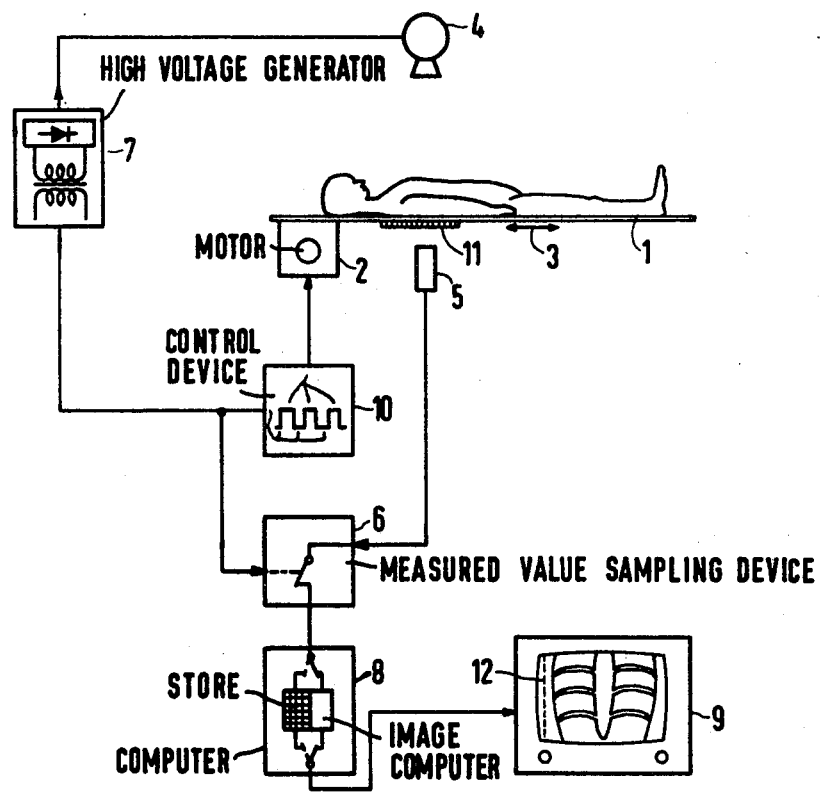
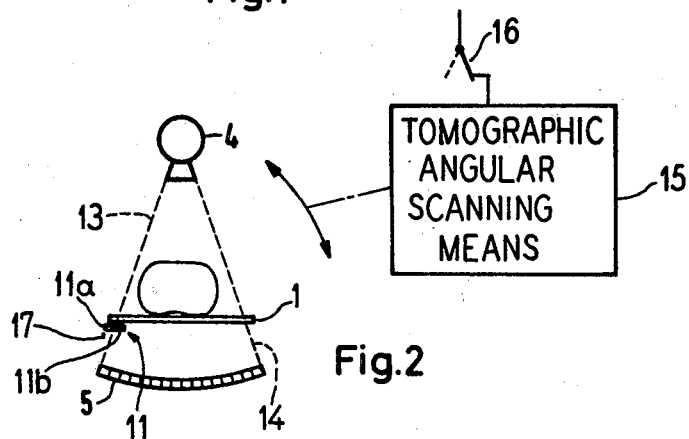

TOMOGRAPHIC X-RAY APPARATUS FOR THE PRODUCTION OF TRANSVERSE LAYER IMAGES

CROSS REFERENCE TO RELATED APPLICATION

Reference is made pursuant to 37 CFR 1.79 to a continuation application being filed on or about June 29, 1979, and directed to apparatus for automatically producing an x-ray shadow image with the tomographic equipment of the present disclosure.

BACKGROUND OF THE INVENTION

This invention relates to a tomographic X-ray apparatus for the production of transverse layer images of an exposed object, consisting of a patient's support, an X-ray measuring arrangement with an X-ray source, which generates a bundle of X-rays penetrating the exposed object and of which the cross sectional extent perpendicular to the plane of the layer is equal to the thickness of the layer, for example, and a radiation receiver which ascertains the radiation intensity beyond the object by scanning the projected bundle of rays, and a driving device for the measuring arrangement including a pivot mounting for accommodating rotational movements of the X-ray measuring arrangement, the apparatus further including a measurand converter for the conversion of the signal supplied by the radiation receiver into a tomographic image.

For detecting the layer image, the rotational movements may take place through equidistant angular amounts, each in alternating sequence with a displacement of the measuring arrangement along a straight line perpendicular to the central ray of the bundle of X-rays, when a single detector is used as the radiation receiver. Alternatively, it is possible to dispense with the displacements along a straight line path if the radiation receiver is built up of a multiplicity of ray detectors whose signals are simultaneously processed by the measurand converter. For example, the X-ray beam may be fan-shaped and the detectors may be arranged in succession so as to simultaneously receive the X-ray energy after traverse of paths of equal length.

A tomographic X-ray apparatus of this kind is described in U.S. Pat. No. 3,974,388 issued Aug. 10, 1976. The exact positioning of a patient and the accurate choice of the transverse layer to be imaged is difficult, because it is difficult to ascertain the exact transverse layer of the body which is being scanned by the X-ray energy. The cited patent represents a tomographic apparatus seeking to facilitate the desired exact positioning of the patient wherein markings are applied relative to a precisely determined patient location such as the eye-ear line. In this apparatus, for example, an adhesive band may be adhered to the side of the patient's head, having a scale disposed longitudinally of the patient which is utilized in conjunction with a light visor to enable a precise determination of the position of the scanning layer relative to the reference line.

SUMMARY OF THE INVENTION

The invention has for its object to design a tomographic X-ray apparatus of the kind mentioned such that an exact positioning of the patient in relation to the measuring arrangement can be readily effected.

In accordance with the invention, this object is achieved by virtue of the fact that there are provided means for producing a relative displacement between the measuring arrangement and the patient's support in the longitudinal direction of the latter during the processing of the signals supplied by the radiation receiver, the measuring arrangement being locked against rotation, and by virtue of the fact that there is connected to the measurand converter a television display unit for reproducing the X-ray shadow image of the patient, which is computed by the measurand converter from the signals of the radiation receiver over the range of longitudinal displacement. In the tomographic X-ray apparatus according to the invention there is provided with the aid of the radiation receiver an X-ray image which is similar to a conventional radiograph. This X-ray image which is reproduced on the television display unit makes it possible to select with accuracy the desired transverse layer which is to be measured by means of the tomographic measuring arrangement. Simple positioning of the patient in relation to the measuring arrangement is possible if there is mounted on the patient's support a scale which is reproduced on the television display unit together with the X-ray shadow image.

Other objects, features and advantages of the present invention will become apparent from the following detailed description taken in conjunction with the accompanying sheet of drawings.

BRIEF DESCRIPTION OF THE DRAWINGS

FIG. 1 shows those parts of a tomographic X-ray apparatus according to the invention which constitute the essential apparatus components of the invention and which are utilized in the practice of the inventive method; and FIG. 2 shows a detail of the tomographic apparatus according to FIG. 1, the view of FIG. 2 being taken in the transverse plane being scanned by the apparatus of FIG. 1.

DETAILED DESCRIPTION

In FIG. 1 there is shown a patient's support 1 which is adapted to be subjected to longitudinal reciprocating movement in the direction indicated by double arrow 3 by means of a motor 2. For producing X-ray images, there is provided a measuring arrangement consisting of an X-ray tube 4 and a radiation receiver 5. The output of the radiation receiver 5 is connected to a measurand reading unit 6 so that the analog readings from the radiation receiver 5 can be converted to digital form and stored. The output of the radiation receiver 5 may be sampled by means of the reading unit 6 during intervals corresponding to the intervals of energization of the high voltage generator 7 which supplies the X-ray tube 4. For the sake of diagrammatic illustration, the measured value sampling device 6 is shown as supplying each sample of the readings from the radiation receiver 5 selectively to an image computer component or a "store" component of computer 8. For the case where the measured value sampling device 6 stores the analog readings from receiver 6 in analog form only for the time interval required to convert such analog readings to digital form, during normal tomographic scanning, the digital readings so obtained by means of the sampling device 6 may be supplied to the image computer of component 8 after each energization of the X-ray source 4 for storage in a suitable computer memory. The "store" component for use in locating the precise region to be tomographically scanned, may comprise a RAM buffer memory and circulating memory as shown in the tenth figure of an article entitled "The Siretom, a Computerized Transverse Axial Tomograph for Brain Scanning", of which the present applicant is one of the authors, said article being found in the publication *Electromedia*, number 2-3 of 1975, pages 48 through 55. The "store" of component 8 may store each set of readings from receiver 5 corresponding to each patient longitudinal position at a respective row of storage cells so that the rows may be read out in step with the horizontal deflection rate of the television display unit 9.

In addition, FIG. 1 illustrates a control device 10 which controls the longitudinal driving motor 2 and also the measured value sampling device 6 and the high voltage generator 7.

According to the embodiment of FIG. 2, the measuring arrangement 4, 5 may comprise an X-ray tube 4 which generates a fan-shaped bundle of X-rays having lateral margins as indicated at 13, 14, the X-ray energy being incident upon the radiation receiver 5 which is curved about the focus of the X-ray tube 4. The radiation receiver 5 consists of a detector bank comprising a multiplicity of detector units, for example 242 detectors, so that in the radiation of the patient at a given longitudinal position, 242 individual measurands or readings are obtained. For producing a transverse layer image, the unit 4, 5 is rotated under the control of scanning means 15. FIG. 2, about the patient in a plane perpendicular to the length of the patient support 1 and in the plane of the bundle of rays defined by marginal paths 13, 14 in FIG. 2. The output signals of the irradiation receiver 5, which are supplied for each angular position of the measuring arrangement 4, 5, are applied by the measurand-reading unit 6 to the computer 8 which computes therefrom in the known manner a transverse layer image.

For the exact positioning of the patient longitudinally in relation to the measuring arrangement 4, 5 there is provided on the patient support 1 a scale 11 having divisions which can be reproduced by X-rays. Before the actual production of a transverse layer image, the unit 4, 5 is restricted to a limited angular relationship, such as the particular single angular relationship indicated in FIG. 2, as by opening switch 16 to disable the angular scanning means 15, FIG. 2, and the patient support 1 is shifted with the patient so as to cover the longitudinal extent of the patient which includes the particular transverse layer to be located. During the longitudinal displacement by means of the motor 2, the X-ray tube 4 is pulsed and the radiation receiver 5 is read for each such X-ray pulse. There is therefore obtained for predetermined longitudinal positions of the patient support 1 relative to the measuring arrangement 4, 5 measurands or readings which characterize the attenuation of the X-radiation in its passage through the patient. The "store" of computer 8 stores the successive sets of readings as a basis for generating an X-ray shadow image when the stored values are reproduced on the display unit 9 as is indicated in FIG. 1.

Each set of readings from the receiver 5 for a given longitudinal position of the patient relative to the apparatus 4, 5 is utilized to produce an image line extending horizontally on the display unit 9. The number of image dots per image line is equal to the number of detectors in the radiation receiver, so that each horizontal line may have a resolution of 242 dots for the case where there are 242 individual detectors within the receiver 5 as described with respect to FIG. 2. The frequency of the turn-on pulses supplied by control device 10 to the high voltage generator 6 and the speed of operation of motor 2 in driving the support 1 in the direction of arrow 1 are so correlated to one another that the positional resolution in the longitudinal direction corresponds substantially to that which can be provided by the number of detectors in the radiation receiver 5 with respect to the transverse direction. Thus, the control device 10 may supply a turn-on pulse to the high voltage generator at successive longitudinal positions of the patient support 1 relative to the measurement apparatus 4, 5 which are separated by one millimeter, for example. A scale 11, FIG. 2, with suitable scale divisions may be detachably secured at any selected position along the length of support 1 for movement therewith. By way of example, the scale 11 is shown with a section 11a outside the beam path 13, 14 and a section 11b just within a margin 13 of the X-ray energy impinging on the detectors of receiver 5. By storing the readings from the detectors aligned with the scale 11 and storing such readings for each successive longitudinal position, the scale 11 is simultaneously produced in the television image as a marking means 12, FIG. 1. This enables the patient to be readily positioned longitudinally in relation to the measuring arrangement 4, 5. With the aid of the television image, it is possible to identify a particular desired point of the scale 11 and to position this point relative to a fixed reference mark 17 cooperating with the section 11a of scale 11 which has the illustrated visible divisions aligned with those of section 11b which produce the divisions of marking means 12. Thereafter, a transverse layer tomographic image of the chosen region may be formed in the conventional manner.

It is also possible within the scope of the invention to use a single detector as the radiation receiver instead of a bank of detectors if the unit 4, 5 is so arranged as to be transversely displaceable for each relative longitudinal position of the patient to the unit 4, 5. Where a single detector is utilized for the receiver 5, the readings from the detector for the successive transverse positions would be stored as a set of readings, for example each reading being converted to digital form prior to storage. The successive sets of readings so stored would then represent information with respect to successive longitudinal portions of the patient as in the example using the arrangement of FIG. 2 and would be displayed exactly as shown in FIG. 1.

In the embodiment described with reference to FIG. 2, the pulsing of the X-ray tube 4 takes place with the patient's support 1 in predetermined longitudinal positions, that is to say the successive turn-on pulses are supplied to the X-ray generator 7 from the control device 10 at predetermined longitudinal positions of the patient's support 1.

It is also conceivable within the scope of the invention for the support 1 to be fixedly located and for the measuring arrangement 4, 5 to be arranged to be displaced in the longitudinal direction of the support 1 both for producing a synoptic radiographic picture and for the subsequent selection of a specific longitudinal position relative to the patient for scanning to produce the transverse layer or tomographic image.

The computer 8 comprises a store which stores the signals corresponding to an image line which signals are supplied to the store from the radiation receiver 5 via the measured value sampling device 6. The store may have a series of storage locations for the set of readings corresponding to each longitudinal position of the patient, and the number of such series of storage locations may then correspond to the number of detectors of radiation receiver 5, FIG. 2. Thus, after the successive sets of readings are stored by means of the store component of computer 8, the desired synoptic image can be reproduced on the television display unit 9.

For the reproduction of a synoptic exposure from the store component of computer 8, no actual image computation takes place so that the image computer component of computer 8 is not utilized during the generation of the longitudinally extensive radiographic image. The computer store of component 8 for purposes of generating the radiographic image has a number of image stores which is equal to the number of image lines times the number of image dots per image line. For the example of FIG. 2, as previously mentioned, each image line store may comprise 242 storage cells. For reproducing a synoptic exposure, there takes place at the commencement of the displacement of the support 1 by means of the motor 2 a change-over of the computer input that is to say a disconnection of the image computer component of computer 8 and a connection of the computer input to the described store component of computer 8. In this case, the display unit 9 is also disconnected from the image computer component of computer 8 and connected to said store component at its input for displaying the radiographic or synoptic image as specifically illustrated in FIG. 1 including the scale image 12.

The control device 10 is so constructed that it turns on the motor 2 and the X-ray generator 7 pulse-wise. Therefore, the support motor 2 is first turned on or pulsed for carrying out a displacement step of the support 1. For this purpose, the motor 2 may be a conventional stepping motor which indexes a desired longitudinal increment for each pulse supplied thereto. After completion of this longitudinal displacement step, the X-ray tube 4 is turned on by means of the control device 10 supplying a turn-on pulse to the X-ray generator 7 so as to produce an X-ray pulse of desired duration. The support motor 2 then receives a further turn-on pulse for carrying out a further displacement step of the support 1; thereafter, the X-ray tube 4 is turned on by way of the X-ray generator, and so on. The control device 10 thus comprises a simple sequence timer circuit which alternately supplies control pulses to motor 2 and to high voltage generator 7 during the storage of the successive sets of readings from the receiver 5.

The measurand-reading unit 6 is shown as including a switch which connects the output of the ray receiver 5 to the input of the computer 8 each time it receives at its left-hand input a pulse from the control device 10 signifying that the X-ray tube 4 has been turned on. Thus, a sample of suitable duration of the output from the radiation receiver 5 for each detector shown in FIG. 2, for example, is transmitted to the store of component 8. Of course, the switch of component 6 is of an electronic nature. If the store of component 8 is a digital storage, then component 6 may include a suitable analog accumulator for the respective readings from the detectors and suitable analog to digital circuitry for converting the readings to digital form and supplying them to the store of component 8.

Supplementary Discussion

Simply for the sake of example, the radiation receiver 5 may comprise a row of semiconductor diodes presenting respective generally narrow rectangular edge faces to the impinging radiation, a fluorescent layer being interposed or sandwiched between every two diodes and at the opposite ends of the row of diodes. In such a radiation receiver, the X-radiation strikes the fluorescent layers at the relatively narrow generally rectangular edges thereof and causing each fluorescent layer to emit visible light in one or both lateral directions such that the impinging radiation produces a corresponding current flow in the respective associated semiconductor diodes. A semiconductor X-ray detector of this type is disclosed in German patent application P 26 22 655.1 filed May 20, 1976 wherein the inventors are the present applicant, Dr. Gunter Luderer and Burghard Weinkauf, such case being identified by the assignee reference number VPA 76 P 5058.

In carrying out the method of the present invention with a semiconductor X-ray detector of the type illustrated in FIG. 2, the scale 11 is fixed to the patient support 1 along the longitudinal extent of the patient within which the scanning layer is to be located. The support 1 with the patient thereon then is placed in an initial position, with the X-ray beam path 13, 14 arranged to impinge at one longitudinal end of the scale 11 and the motor 2 set to index the support 1 so as to progressively move the scale 11 together with the patient through the scanning region. The measured value sampling device 6 is placed in the operating mode such that the switch of component 6 is normally opened but is closed for a suitable interval in response to each pulse from the control device 10. Similarly, the computer component 8 is switched over so that the computer input is connected with the store of component 8 utilized to provide storage for the successive sets of readings from receiver 5. The control device 10 is now turned on and proceeds to alternately supply control pulses to the generator component 7 and sampling device 6 on the one hand, and to the stepping motor 2 on the other hand. Thus, during each energization of the X-ray source 4, a suitable sample of the readings from the detectors of receiver 5 is stored within the store component of computer 8, whereupon the motor 2 is energized to produce a longitudinal indexing movement, the sampling device 6 and generator 7 then again being pulsed, and so on. When the successive sets of readings from receiver 5 have been stored in this way, the stored values can be processed as described in detail in the aforementioned *Electromedica* article, but in such a manner that each set of stored readings is scanned in synchronism with the line rate of the display device 9 so that each set of readings appears as a horizontal line on the display screen as is illustrated in FIG. 1. The visual scale section 11a may have fine divisions corresponding to the vertical resolution of the image to be displayed, for example 242 divisions with a spacing corresponding to the horizontal resolution afforded by the detector units of the receiver 5 of FIG. 2, while scale 11b may have somewhat coarser divisions only, so as to be readily discriminated when displayed at 12 on the display screen. In this way, the patient can be conveniently positioned with an accuracy generally corresponding to the longitudinal resolution of the tomographic scanning system.

It will be apparent that many modifications and variations may be effected without departing from the scope of the novel concepts and teachings of the present invention.

I claim as my invention:

1. The method of aligning a patient with respect to tomographic X-ray apparatus which includes an X-ray tomographic scanner apparatus for scanning a transverse region from successsive angular positions about said region for defining a tomographic image, said method comprising:

(a) restricting the scanner apparatus to a single angular position, (b) moving a patient longitudinally relative to the scanner apparatus while the scanner apparatus remains in said single angular position such that the patient is scanned at successive longitudinal positions offset from each other longitudinally of the patient but is only scanned from the single angular position, (c) storing respective sets of readings from the scanner apparatus for the successive longitudinal positions with the scanner apparatus in said single angular position thereby to provide the data for a graphic display wherein the sets of readings are the basis for successive lines of varying visual characteristics on the display, the stored sets of readings thereby defining a general radiographic view representing a longitudinally extensive image useful in the precise positioning of the patient relative to the tomographic X-ray apparatus, and (d) displaying the stored sets of readings as successive lines of a longitudinally extensive shadow image of the patient.

2. The method of aligning a patient with respect to tomographic X-ray apparatus which includes an X-ray tomographic scanner apparatus for scanning a transverse region from successive angular positions about said region for defining a tomographic image, said method comprising:

(a) moving a patient longitudinally relative to the scanner apparatus while the scanner apparatus is restricted to a limited angular relationship such that the patient is scanned from the limited angular relationship only but at successive longitudinal positions offset from each other longitudinally of the patient, (b) storing respective sets of readings from the scanner apparatus for the successive longitudinal positions thereby to provide the data for a graphic display wherein the sets of readings are the basis for successive lines of varying visual characteristics on the display, the stored sets of readings thereby defining a general radiographic view representing a longitudinally extensive image useful in the precise positioning of the patient relative to the tomographic X-ray apparatus for the purpose of a subsequent scanning not restricted to the limited angular relationship but relating to a tomographic layer having greatly restricted longitudinal extent, and (c) moving a scale having subdivisions corresponding to the restricted longitudinal extent of a tomographic layer to be scanned longitudinally with the patient relative to the tomographic scanner apparatus with the scale positioned such that the beam of the tomographic scanner apparatus impinges on the scale and produces readings pertaining thereto in each of the successive longitudinal positions, and storing such readings as part of the respective sets of readings so that the stored sets of readings define successive lines of varying visual characteristics each including a longitudinal segment of the scale, the stored sets of readings thereby defining an extended longitudinal view of the scale in accurate transverse alignment to the general radiograph representing a longitudinally extensive image of the patient.

3. Tomographic apparatus for the production of transverse layer images of an exposed subject, comprising a patient's support, an X-ray measuring arrangement including an X-ray source which produces a beam of X-ray energy for penetrating the exposed subject with respect to a transverse plane, and a radiation receiver which provides readings which are measures of the radiation intensity of the transmitted beam, scanning means coupled with the source and receiver for producing rotational movements through a wide range of angular relationships so as to generate a sufficient number of sets of readings to define a tomographic layer image, characterized in that longitudinal drive means are provided for producing relative longitudinal movement between the measuring arrangement and the patient's support in the longitudinal direction of the latter during storage of the readings from the radiation receiver, control means coupled with the longitudinal drive means for producing longitudinal movement through successive longitudinal positions while the measuring arrangement is retained in a restricted angular relationship so as to generate sets of readings from the radiation receiver with reference to the successive longitudinal positions, means providing for the storage of sets of readings relating to successive longitudinal positions for defining an X-ray shadow image of the patient having a substantial transverse extent and having a longitudinal extent corresponding to the range of longitudinal movement produced by said longitudinal drive means during the storage operation, the patient's support having a scale with markings thereon substantially corresponding to the incremental longitudinal distance between the successive longitudinal positions where the successive sets of readings are taken, and television display means for reproducing the successive sets of stored readings as successive lines of an X-ray shadow image of the patient, and for displaying the scale along with the X-ray shadow image of the patient.

* * * * *